United States Patent [19]
Sinnott

[11] Patent Number: 5,945,106
[45] Date of Patent: *Aug. 31, 1999

[54] MONTOXIC EXTRACT OF *LARREA TRIDENTATA* AND METHOD OF MAKING THE SAME

[75] Inventor: Robert A. Sinnott, Chandler, Ariz.

[73] Assignee: Larreacorp, Ltd., Chandler, Ariz.

[*] Notice: This patent is subject to a terminal disclaimer.

[21] Appl. No.: 09/152,054

[22] Filed: Sep. 11, 1998

Related U.S. Application Data

[63] Continuation of application No. 08/726,686, Oct. 7, 1996, Pat. No. 5,837,252
[60] Provisional application No. 60/064,674, Oct. 20, 1997, provisional application No. 60/064,802, Oct. 20, 1997, provisional application No. 60/064,803, Oct. 20, 1997, provisional application No. 60/064,804, Oct. 20, 1997, provisional application No. 60/064,805, Oct. 20, 1997, and provisional application No. 60/020,946, Jul. 1, 1996.

[51] Int. Cl.⁶ .................................................. A01N 65/00
[52] U.S. Cl. ............................................................ 424/195.1
[58] Field of Search ........................ 424/195.1; 514/731, 514/885, 934

[56] References Cited

U.S. PATENT DOCUMENTS

| | | | |
|---|---|---|---|
| 2,382,475 | 8/1945 | Gisvold | 568/729 |
| 4,765,927 | 8/1988 | Nomura et al. | 252/400.2 |
| 4,774,229 | 9/1988 | Jordan | 514/25 |
| 4,880,637 | 11/1989 | Jordan | 424/641 |
| 5,276,060 | 1/1994 | Neiss et al. | 514/731 |

OTHER PUBLICATIONS

Timmermann "Practical uses of Larrea in Creosote Bush," in "Biology and Chemistry of Larrea in the New World Deserts," Mabry et al. eds. (1977) (Dowden, Hutchinson and Ross: Pennsylvania) pp. 252–276.

Gnabre et al. "Isolation of anti–HIV lignans from Larrea tridentata," Tetrahedron (1995) 51(4(:12203–12210.

*Primary Examiner*—Jean C. Witz
*Assistant Examiner*—Susan M. Hanley
*Attorney, Agent, or Firm*—David K. Benson

[57] ABSTRACT

A nontoxic, therapeutic agent having pharmacological activity comprising concentrated extract of *Larrea tridentate* plant material and ascorbic acid is made by a process in which the plant material is extracted using an organic solvent, and is then saturated with ascorbic acid to reduce the toxic NDGA quinone, which naturally occurs in the plant material, to NDGA itself. Additional amounts of ascorbic acid are added to the extract to inhibit the natural oxidation of the NDGA into the toxic NDGA quinone in vivo, or during processing or storage. The resulting extract is useful in the treatment of viral diseases caused by viruses from the Herpesviridae family or viruses which require the Sp1 class of proteins to initiate viral replications. The resulting compound can also be used as an anti-inflammatory when the inflammatory diseases are mediated by the effects of leukotrienes. The listed reducing agents can also be used to stabilize NDGA as a therapeutic agent or a food additive.

19 Claims, 5 Drawing Sheets

MONTOXIC EXTRACT OF *LARREA TRIDENTATA* AND METHOD OF MAKING THE SAME

This application is a continuation-in-part of U.S. patent application Ser. No. 08/726,686, now U.S. Pat. No. 5,837,252, which claims benefit to U.S. provisional application Ser. No. 60/020,946, filed Jul. 1, 1996, and further claims priority benefits of provisional application Ser. Nos. 60/064,674; 60/064,802; 60/064,803; 60/064,804; and 60/064,805, all of which were filed Oct. 26, 1997.

FIELD OF THE INVENTION

The present invention relates generally to a nontoxic extract of *Larrea tridentate* plant material having therapeutic value and a method of making the same. The present invention also relates to the field of nontoxic, stable NDGA products used as food additives and therapeutic agents.

BACKGROUND OF THE INVENTION

*Larrea tridentate*, also known as *Larrea divaricata*, Larrea, chaparral, or creosote bush, is a shrubby plant which dominates some areas of the desert southwest in the United States and Northern Mexico as well as some desert areas of Argentina. Tea made from the leaves of *Larrea tridentate* has long been used in folk medicine to treat digestive disorders, rheumatism, venereal disease, sores, bronchitis, chicken pox, and the common cold.

According to Masayuki Sakakibara, et al., *Flavonoid Methyl Ethers on the External Leaf Surface of Larrea Tridentate and L. Divaricata* in PHYTOCHEMISTRY, vol. 15, pp. 727–731 (Pergamon Press 1976), the disclosure of which is incorporated herein by reference, the natural products on the surface of the *Larrea tridentate* leaves, the leaf resin, constitutes approximately 10–15% of the dry weight of the leaves and is composed of approximately 50% nordihydroguaiaretic acid ("NDGA") and related lignans, and 50% flavonoids. NDGA, extracted from *Larrea tridentate* by an alkaline extraction method (U.S. Pat. No. 2,382,475, incorporated herein by reference) and produced synthetically (U.S. Pat. No. 2,644,822, incorporated herein by reference) was used as an antioxidant in edible fats, butter, oils and oleaginous materials (U.S. Pat. No. 2,373,192, incorporated herein by reference), until the GRAS (Generally Recognized As Safe) status of NDGA was revoked after animal studies revealed evidence of kidney toxicity resulting from the ingestion of NDGA.

NDGA is known as a powerful antioxidant compound. However, NDGA can itself be oxidized to toxic oxidation products by chemical means or by oxidation during processing and storage. A highly reactive and toxic oxidation product of NDGA is nordihydroguaiaretic acid ortho di-a-b-unsaturated quinone ("NDGA quinone"), which according to T. J. Mabry et al., *The Natural Products Chemistry of Larrea* in CREOSOTE BUSH: BIOLOGY AND CHEMISTRY OF LARREA IN THE NEW WORLD DESERTS, ch. 5, pp. 115–133 (Dowden, Hutchinson and Ross, Pennsylvania 1977) (incorporated herein by reference), occurs in Larrea and Larrea extracts and probably serves as a toxin to protect the plant from being eaten by herbivores. According to a recent report by FDA scientists (W. R. Obermeyer et al., *Chemical Studies of Phytoestrogens and Related Compounds in Dietary Supplements: Flax and Chaparral*, 208 PROC. SOC. EXP. BIOL. MED., pp. 6–12 (1995), the disclosure of which is incorporated herein by reference), NDGA quinone is found in chaparral (*Larrea tridentate*) and is suspected to be a causative agent of the toxic effects associated with consumption of chaparral products.

NDGA is the dominant lignan present in *Larrea tridentate*. NDGA is known to possess a variety of biological effects including anti-tumor activity, enzyme inhibition activity and antimicrobial activity according to W. Donald MacRae & G. H. Neil Towers, *Biological Activities of Lignans*, PHYTOCHEMISTRY, vol. 23, pp. 1207–1220 (Pergamon Press 1984) (incorporated herein by reference). Additionally, NDGA and other antioxidants have been shown to be potent inhibitors of the human immunodeficiency virus type 1 (HIV) transcription. The mode of action of this anti-HIV activity was suggested to be due to the potent antioxidant activity of NDGA inhibiting a redox regulated signal transduction pathway leading to production of HIV virus.

More recently, three scientific articles, John N. Gnabre et al., *Inhibition of human immunodeficiency virus type 1 transcription and replication by DNA sequence-selective plant lignans*, PROC. NATL. ACAD. SCI., USA, vol. 92, pp. 11239–11243 (November 1995); John Gnabre et al., *Characterization of Anti-HIV Lignans from Larrea tridentate*, TETRAHEDRON, vol. 51, pp. 12203–12210 (1995); and John Noel Gnabre et al., *Isolation of anti-HIV-1 lignans from Larrea tridentate by counter-current chromatography*, JOURNAL OF CHROMATOGRAPHY A, vol. 719, pp. 353–364 (1996), the disclosure of all three articles being incorporated herein by reference, demonstrate that at least two lignans isolated from *Larrea tridentate*, NDGA and 3-O-methyl nordihydroguaiaretic acid ("Mal. 4") inhibit transcription and replication of human immunodeficiency virus type 1 by a novel mechanism. This elucidated mechanism of anti-HIV activity is thought to be due to the ability of the two identified *Larrea tridentate* lignans, NDGA and Mal. 4, to interfere with the binding of the Sp1 protein to Sp1 binding sites in the HIV long terminal repeat (HIV-LTR). According to this theory, by inhibiting Sp1 binding in the HIV-LTR, the promoter activity of the HIV-LTR is eliminated so that HIV transcription, HIV Tat-regulated transactivation and HIV replication do not occur. It is further theorized by the authors that viruses other than HIV, which require binding of Sp1 protein in promoter-containing Sp1 binding sites to initiate viral replication, might also be inhibited by the anti-HIV lignans isolated from *Larrea tridentate* and that this class of lignans, in general, may possess a broader antiviral action of important interest.

Also, in a recent article, Anneke K. Raney & Alan McLachlan, *Characterization of the Hepatitis B Virus Large Surface Antigen Promoter Sp1 Binding Site*, VIROLOGY, vol. 208, pp. 399–404 (1995), binding sites for the transcription factor Sp1 have been identified in the DNA promoter regions of at least two important viral genes of the Hepatitis B virus (HBV) which may be involved in the coordinate regulation of HBV transcription by transcription factor Sp1.

Kaposi's Sarcoma, a cancer that frequently occurs among AIDS patients, has recently been implicated to be caused by a new herpes virus, human herpes virus-8 (HHV-8). See Roland G. Nador et al., *Primary Effsion Lymphoma: A Distinct Clinicopathologic Entity Associated With the Kaposi's Sarcoma—Associated Herpes Virus*, BLOOD, vol. 88, no. 2, pp. 645–656 (Jul. 15, 1996), incorporated herein by reference. See also, Matt Crenson, *Kaposi's Sarcoma is tied to herpes*, THE PHILADELPHIA INQUIRER, p. A4 (Jul. 31, 1996), and Lawrence K. Altman, *Aids Cancer Said to Have Viral Source: Breakthrough Seen in Kaposi's Sarcoma*, NEW YORK TIMES § A, p. 22 (Feb. 1, 1995), incorporated herein by reference. Antiviral therapy for immunocompromised individuals is difficult to administer, as current drugs such as acyclovir are not considered practical treatments when the immune system is compromised (New England Journal of Medicine, 1992, Vol. 327, No. 11, 782–789).

Cancerous cells are commonly treated using various forms of chemotherapy, with some degree of success in many patients. Human glioma cells are among the brain tumor cells that have been treated using chemotherapy with limited success. Human glioma cells can be derived from a glioblastoma multiforme and cultured to become a drug resistant line. However, these same cells have survived treatments of 70 ug/ml BCNU, currently, the most common chemotherapeutic agent used in the treatment of glioblastoma multiforme.

Estrogens are known to promote the growth of breast cancers. Therefore, inhibiting the production of estrogens through the use of aromatase inhibitors is an important pharmaceutical accomplishment toward the treatment and/or prevention of breast cancers. Cancer Research 53, 4563–4566, Oct. 1, 1993. Lignans and flavonoids have been shown to be competitive inhibitors of human preadipocyte aromatase. Certain naturally-occurring lignans and flavonoids have been shown to be moderate inhibitors of aromatase with K; values of between 1.3 and 27.2 micromolar concentration. These natural compounds, while not as powerful as some synthetic aromatase inhibitors, are similar in potency to some pharmaceutically useful aromatase inhibitors such as glutethimide, which has a $K_i$ value of 0.5 micromolar concentration. Aromatase functions in the conversion of androstene and testosterone to estrogens. In this capacity, lignans and flavonoids function as competitive inhibitors for the binding of the aromatase substrates, androstene and testosterone to the active site of the aromatase enzyme. Inhibition of aromatase enzyme activity, resulting in reduction of estrogen synthesis and subsequent decrease in circulating plasma estrogen levels, is thought to contribute to the prevention of estrogen-dependent cancers, such as breast cancer. (J. Steroid Biochem. Molec. Biol. Vol. 50, No. 3/4, pp. 205–212, 1994; J. Steroid Biochem. Molec. Biol. Vol. 57, No. 3/4, pp. 215–223, 1996; J. Steroid Biochem. Molec. Biol. Vol. 37, No. 2, pp. 257–260, 1990.)

Herpes zoster, also known as shingles, afflicts approximately 300,000 to 500,000 people each year in the United States. Herpes zoster most often affects elderly and immunocompromised patients, such as those with AIDS, cancer, infections, physical trauma or those undergoing certain drug therapies. It is estimated that zoster will occur at some time in ten to 20 percent of the population. Men and women are affected equally by zoster and there are no apparent seasonal variations or racial predilections. Herpes zoster occurs at a constant rate of two to three cases per 1,000 between 50 and 80 years and increases again to 10 cases per 1,000 in persons over 80 years of age.

The etiological role of varicella-zoster virus in herpes zoster, which occurs predominantly in persons over the age of 20, was confirmed in 1984 by molecular biology methods. Herpes zoster occurs due to the reactivation of the varicella-zoster virus that has been dormant in the basal root ganglia. Studies of acute herpes zoster have shown that the dorsal root ganglia sustain the brunt of the damage due to viral reactivation and replication. The damage is accompanied by localized acute inflammation, tissue necrosis and often hemorrhaging. In more severe cases, inflammation can spread to adjacent motor and sensory roots. In exceptional cases, inflammation may spread to anterior and posterior horns or posterior columns.

Herpes zoster is usually present as a painful, unilateral vesicular eruption within a single dermatotome. In young, immunocompetent individuals, the course of zoster is usually benign. In elderly patients, however, acute neuritis and postherpetic neuralgia (PHN) may develop. Severe cases of zoster and PHN can be debilitating. Immunocompromised persons are at risk for more serious disease and increased morbidity. PHN is usually defined as pain persisting for more than a month after the date of the original zoster eruption. Overall, about 10% of patients presenting with an acute case of herpes zoster will subsequently get PHN. A third of patients with PHN will still have pain persisting a year or more later. The development and persistence of PHN is greatly increased in elderly patients; almost 50% of those over 70 years may be so afflicted. (The New England Journal of Medicine, 1994, Vol. 330, No. 13, p. 896–900; afp Practical Therapeutics, 1991, Vol. 44, No. 1, p. 203–210). Postherpetic neuralgia is most commonly associated with herpes zoster although neuralgia may be associated with other types of herpes virus infections.

Besides herpes zoster, other members of the herpes virus family that may cause human disease include herpes simplex 1 and herpes simplex 2, cytomegalovirus (CMV), Epstein-Barr virus, human herpes virus 6, and human herpes virus 8. New members of the human herpes virus class continue to be discovered and undoubtedly many more exist in the global population. Recently, the inflammatory process associated with Alzheimer's disease has been linked with the presence of herpes simplex virus in the brain of susceptible individuals (The Lancet, 1997, Vol. 349, p. 241–244). Human herpes virus 6 has recently been linked to multiple sclerosis (Proceedings of the National Academy of Sciences, Vol. 92, p. 7440–7444; National Multiple Sclerosis Society Research Highlights, Summer/Fall 1997, p. 4–6). Cytomegalovirus (CMV) has been linked with the inflammatory process which may lead to hypertension, arteriosclerosis, atherosclerosis and coronary artery disease. Epstein-Barr virus has been linked with human cancers including, Burkitt's lymphoma, naspharyngeal cancer and B-lymphomas (Science, 1991, Vol. 254, p. 1167–1173).

For diseases caused by herpes virus infections including, herpes zoster, herpes simplex and Kaposi's sarcoma, antiviral agents such as acyclovir, valciclover, famiciclover, cytarabine, idoxuridine, and vidarabine may be indicated (The New England Journal of Medicine, 1992, Vol. 327, No. 11, p. 782–789; afp Practical Therapeutics, 1991, Vol. 44, No. 1, p. 203–210; The Lancet, 1990, Vol. 336, p. 537–538; Emergency Medicine, April 1997, 125–126.) The primary action of these drugs is to inhibit viral DNA synthesis. Vidarabine and acyclovir are both approved by the U.S. Food and Drug Administration for the treatment of zoster. Most clinicians consider acyclovir to be the drug of choice because of its relatively low toxicity. Acyclovir has been shown to accelerate lesions healing and lessen the pain of the infection's acute stage.

The treatment goals in patients with herpes zoster are to minimize discomfort, shorten the duration of symptoms, prevent dissemination and other complications, and prevent or minimize postherpetic neuralgia (afp Practical Therapeutics, 1991, Vol. 44, No. 1, p. 203–210). Many currently used antiviral medications for herpes virus infections, including acyclovir, do not appear to significantly reduce the incidence of duration of postherpetic neuralgia, which can occur in relatively healthy and immonocompetent elderly persons (The New England Journal of Medicine, 1992, Vol. 327, No. 11, p. 782–789; The Lancet, 1990, Vol. 336, p. 537–538). Recently, it has been demonstrated that corticosteroids (i.e. prednisolone or prednisone), which function as anti-inflammatory agents, in combination with antiviral therapy, can resolve episodes of acute pain and improve quality of life for the elderly immonocompetent patient (The Lancet, 1990, Vol. 336, p. 537–538; Emergency Medicine, April 1997, p. 125–126; Annals of Internal Medicine, 1996, Vol. 125, p. 376–383; Annals of Internal Medicine, 1997, Vol. 126, p. 831–832).

Besides the combination of acyclovir and corticosteroids, other recognized preventions and treatments for postherpetic neuralgia include: tricyclic anti-depressant compounds (i.e. amitirptylene; possibly combined with a neuroleptic agent, i.e. a phenothiazine compound), anticonvulsants compounds (i.e. carbamazepine), neuroaugmentation with topical ethyl chloride spray to control pain, a substance P antagonist (i.e. topically applied capsaicin), transcutaneous nerve stimulation, strong analgesics and narcotics (i.e. acetominophen, codeine), nonsteroidal anti-inflammatory agents (i.e. ibuprofen), topical anti-inflammatory agents (i.e. benzydamine), short courses of corticosteroid therapy (i.e. trimacinolone, prednisolone, prednisone), nerve blocks (i.e. lidocaine, bupivacaine, procaine; possibly combined with a steroid compound or noradrenaline), topical local anesthetics (i.e. Eutectic Mixture of Local Anesthetics) and surgical procedures. It has been noted in the medical literature that no treatment for PHN has proven to be uniformly successful, although some treatments may offer significant benefits. (The Lancet, 1990, Vol. 336, p. 537–538;; afp Practical Therapeutics, 1991, Vol. 44, No. 1, p. 203–210; Herpes Zoster and Post Herpetic Neuralgia, C. P. N. Watson, ed., 1993, Elsevier Science Publishers B. V., Amsterdam, Chapters 12–15).

In addition to corticosteroids, many other anti-inflammatory agents have been identified and are in common use. These include, nonsteroidal anti-inflammatory drugs (NSAIDs), and substances containing certain naturally occurring, anti-inflammatory fatty acids such as gamma-linolenic acid, alpha-linolenic acid and omega-3-fatty acids.

The class of nonsteroidal anti-inflammatory drugs include aspirin, ibuprofen, phenylbutazone and indomethacin as well as others. All the commonly used NSAIDs exert their analgesic and anti-inflammatory effects, at least in part, by inhibition of cyclooxygenase, the enzyme that initiates transformation of arachidonic acid to prostaglandins, prostacyclin and thromboxanes. Currently used NSAIDs are generally safe, well tolerated and effective when properly administered. NSAIDs are widely used for treatment of pain and inflammation and are often formulated with other pharmaceutical agents, such as caffeine or opioids, to achieve specific pharmaceutical effects. Formulations containing NSAIDs are represented in both prescription and over-the-counter drugs.

The anti-inflammatory effects of certain naturally occurring fatty acids, especially the omega-3-fatty acids and gamma-linolenic acid (GLA), are now widely known. (Proceedings of the Nutritional Society, 1996, Vol. 55, p. 737–775; Annals of Nutrition and Metabolism, 1996, Vol. 40, p. 175–182). Arachidonic acid (AA) derived eicosanoids are involved in mediating inflammatory responses. Since omega-3-fatty acids diminish the production of eicosanoid mediators, these fatty acids exert anti-inflammatory activity. Eicosapentaenoic acid (EPA) and docosahexaenoic acid (DHA), which are abundant in fish oils and some marine plant oils, have been shown in numerous studies to exert anti-inflammatory effects. Additionally, the omega-3-fatty acid, alpha-linolenic acid (LNA), which is abundant in some vegetable oils, including flax seed and perilla seed oils, has been shown to possess anti-inflammatory activity.

Gamma-linolenic acid (GLA) is not an omega-3 fatty acid, but rather, it is an omega-6 fatty acid like arachidonic acid (AA). Most, but not all eicosanoids potentiate the inflammatory pathway which leads to inflammatory diseases. The "1-" series prostaglandins produced by the metabolism of gamma-linolenic acid in place of arachidonic acid actually possess anti-inflammatory properties. Additionally, GLA also inhibits the production of inflammatory eicosanoids by competing with arachidonic acid for eicosanoid synthesis enzymes. A particularly rich source of gamma-linolenic acid is evening primrose oil.

Capsaicin, a natural product extracted from hot peppers of the botanical genus Capsicum, has been used in the treatment of postherpetic neuralgia, other types of painful nerve disorders and inflammatory conditions. Hot peppers and their extractives have been used in food products and herbal medicine since ancient times. Extractives of Capsicum peppers contain differing amounts of capsaicin depending on the variety of pepper extracted and the extraction conditions employed. Capsaicin does not necessarily need to be purified from the other components of hot pepper extracts in order to be useful in pharmaceutical preparations. Hot pepper extracts including oleoresins and alcoholic extracts have been used in herbal medicine. The warming or burning sensation evoked by the topical application of capsaicin or an extract of Capsicum peppers may be partially masked by pretreatment or simultaneous application of a topical anesthetic (i.e. lidocaine).

There are many topical anesthetics to choose from which may be formulated with natural or synthetic antiviral agents for treatment of herpes virus infections and the pain associated with them. Two topical anesthetics commonly used in over-the-counter preparations are benzocaine and lidocaine. A naturally occurring topical anesthetic, cocaine, could also be used in place of the synthetic anesthetic compounds although, given the bad reputation associated with widespread abuse of cocaine, use of this compound is questionable in actual practice.

The combination of an effective antiviral therapy with another type of therapy to control the pain and/or inflammation associated with herpes virus infections, such as PHN, has great utility and represents an additional treatment option where, currently, effective treatment options are limited.

Certain flavonoid compounds, especially members of the chemical classes flavones and flavonols can inhibit HIV activation at fairly low concentrations (See , J. William Critchfield et al., *Inhibition of HIV Activation in Latently Infected Cells by Flavonoid Compounds*" in *AIDS Research and Human Retroviruses,* AIDS RESEARCH AND HUMAN RETROVIRUSES, Vol. 12, no. 1, pp. 3946 (1996), incorporated herein by reference). As further cited in Masayuki Sakakibara, et al., *Flavonoid Methyl Ethers on the External Leaf Surface of Larrea Tridentate and L. Divaricata* in PHYTOCHEMISTRY, vol. 15, pp. 727–731 (Pergamon Press 1976), Lariea tridentata contains an abundance of these classes of antiviral flavonoids, particularly methyl ethers of flavonols.

Like many physiologically active chemicals isolated from plant sources, these antiviral lignans and flavonoid compounds appear to work synergistically with other unresolved compounds present in crude extracts of *Larrea tridentate*. The identity and mode of action of these synergistic compounds is unknown but they may facilitate absorption of the antiviral lignans or otherwise enhance the specific physiological, antiviral effects.

NDGA is known to be a potent inhibitor of the enzyme 5-lipoxygenase. One of the enzymatic products of 5-lipoxygenase is 5-hydroperoxyeicosatetraenoic acid (HPETE) which is the precursor compound for the biosynthesis of very potent chemical mediators of inflammation, known as leukotrienes. As detailed in William R. Henderson, *The Role of Leukotrienes in Inflammation*, ANN. INTER. MED., vol. 121, pp. 684–697 (1994), the disclosure of which is incorporated herein by reference, 5-lipoxygenase is limited to a specific number of myeloid cells including: neutrophils, eosinophils, monocytes, macrophages, mast cells, basophils and B-lymphocytes. Leukotrienes are chemicals which induce prolonged muscle contraction, especially in the bronchioles of the lungs, and also increase vascular permeability and attract neutrophils and eosinophils to the site of inflammation. The leukotrienes play a major role in the inflammatory response to injury. Leukotrienes have also been implicated in the pathogenesis of several inflammatory diseases including: asthma, psoriasis, rheumatoid arthritis and inflammatory bowel disease. The role of leukotrienes as mediators of inflammatory diseases makes them attractive targets for therapeutic drugs to treat these diseases.

Many inhibitors of leukotriene synthesis are being developed. Recently, a 5-lipoxygenase inhibitor, Zileuton, was found to be effective in the treatment of asthma during clinical tests (Elliot Israel et al., *Effect of Treatment With Zileuton, a 5-Lipoxygenase Inhibitor, in Patients With Asthma*, JAMA, vol. 275, pp. 931–936 (Mar. 27, 1996), the disclosure of which is incorporated herein by reference). The success of Zileuton underscores the utility and need of therapeutic agents containing 5-lipoxygenase inhibitors in the treatment of inflammatory disease processes, including asthma.

Throughout this specification and claims, viral diseases are intended to include all diseases, attributed to a pathological virus of humans or animals, in which the causative viral agent which requires the Sp1 class of proteins to initiate viral replication, including certain viral agents of venereal diseases such as the Herpes viruses (the Herpesviridae), HSV-1 and HSV-2, viral hepatitis (the Hepadnaviridae) such as hepatitis B, and members of the retrovirus family (the retroviridae) including Varicella-Zoster viruses, cytomegalovirus (CMV), the human T-lymphotrophic viruses 1 and 2 (HTLV-1 and (HTLV-2) the human immunodeficiency viruses 1 and 2 (HIV-1 and HIV-2) and the cancer Kaposi's Sarcoma. Inflammatory diseases, throughout the specification and claims, are intended to include all diseases in which leukotrienes are known to play a major role or have been implicated including: asthma, allergic rhinitis, psoriasis, rheumatoid arthritis, inflammatory bowel disease, inflammatory pain, cystic fibrosis, adult respiratory distress syndrome, glomerulonephritis, inflammation of the skin, and virally induced inflammation (caused by CMV and other members of the Herpesviridae) leading to atherosclerosis/ arteriosclerosis and subsequent coronary artery disease.

In light of the foregoing. background, there exists the need for a commercial method of producing a *Larrea tridentate* extract which contains a high concentration of both the identified antiviral lignans (NDGA and Mal. 4), flavonoids, and a wide variety of other associated organic compounds from the leaf resin, which may contribute synergistic antiviral and lipoxygenase inhibitory activity.

Additionally, for the purpose of toxicological safety, it is of critical importance that the *Larrea tridentate* extract, to be used for medical applications, be processed to reduce the concentration of the toxic compound, NDGA quinone, which is reported to occur naturally in *Larrea tridentate* plant tissues. There is also a need to inhibit the natural production of toxic oxidation products, such as NDGA quinone, in the Larrea tridentata extract during processing and storage of the extract and formulated products and to facilitate the processing of the concentrated extract as either a liquid, slurry, or solid.

Lastly, there is a need for products comprising synthesized NDGA which is stabilized against oxidation into NDGA quinone during processing and storage. Specifically, there exists the need for additional, effective pharmaceutical treatment products for cancer cells, which may include human glioma cells. There is also an existing need for a natural, non-toxic chemical composition formulated from a nontoxic extract of *Larrea tridentate* which would have significant advantages over synthetic chemicals that are used to treat breast cancer. There also exists the need for additional, effective pharmaceutical treatment products for herpes virus infections, which may include pronounced inflammatory reactions, such as postherpetic neuralgia (PHN). Additional value may be added if a combination of antiviral therapy and therapy to control the pain and inflammation associated with herpes viruses could be formulated into convenient topical and oral usage forms. Still, additional value may be added if one or more components of the pharmaceutical composition are naturally occurring substances since natural compounds may offer cost savings, increased customer acceptance and more rapid progression through the testing and marketing process.

SUMMARY OF THE INVENTION

Accordingly, it is an object of the present invention to meet the above described needs and others. It is an object of the present invention to provide a nontoxic extract of *Larrea tridentate* having a high concentration of NDGA. It is a further object of the present invention to provide a nontoxic extract of *Larrea tridentate* containing Mal.4 and other compounds having known or expected, and perhaps synergistic, therapeutic effects.

It is a further object of the present invention to provide such an extract which contains little or no NDGA quinone and which inhibits the production of NDGA quinone in vivo and during processing and storage. It is a further object of the present invention to provide a method of making the above-described extract, and formulations thereof.

It is a further object of the present invention to provide pharmaceutical formulations of the *Larrea tridentate* extract having utility for the treatment of herpes virus infections. It is a further object of the present invention to provide pharmaceutical formulations of the *Larrea tridentate* extract which possess anti-inflammatory and pain relieving qualities in addition to antiviral activity.

It is a further object of the present invention to provide NDGA products for use as food additives or therapeutic agents in which the NDGA is prevented during storage and processing from oxidizing into NDGA quinone.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve the stated and other objects of the present invention, as embodied and described below, the invention may comprise:

A method of preparing a nontoxic extract of *Larrea tridentate* plant material comprising the steps of:

extracting endogenous antiviral and anti-inflammatory lignans and flavonoids and other synergistic compounds from *Larrea tridentate* plant material with a polar solvent, preferably acetone, to produce an extract by recirculating the solvent over the plant material a plurality of times;

filtering the extract;

adding an emulsifying and stabilizing agent, preferably polysorbate 80, to the filtered extract;

reducing the NDGA quinone in the extract with ascorbic acid, ascorbic acid esters (i.e. ascorbyl paiitate), or ascorbic acid salts (i.e. sodium ascorbate), preferably ascorbic acid, by passing the extract through a bed of ascorbic acid powder;

boiling the organic solvent out of the compound; and adding additional amounts of one of the above listed reducing agents to the compound subsequent to the step of reducing.

The present invention may also comprise:

A nontoxic, therapeutic agent comprising:

an extract of *Larrea tridentate* plant material comprising NDGA and Mal.4; and ascorbic acid, ascorbic acid esters (i.e. ascorbyl palmitate), or ascorbic acid salts (i.e. sodium ascorbate).

The present invention may also comprise formulations of the described therapeutic agent in the embodiment of a lotion, liquid, powder or pill. The formulations may be combined with one or more of a corticoid steroid compound, a local anesthetic compound, a non-steroidal anti inflammatory drug, an anti inflammatory fatty acid, and a substance P antagonist.

Where a corticosteroid compound is combined with the formulations including the Larrea genus extract, examples of suitable corticosteroids include amcinonide, betamethasone dipropionate, betamnethasone valerate, clocortolone pivalate, corticosterone, corticosterone 21-acetate, desonide, desoximetasone, diflorasone diacetate, halcinonide, hydrocortisone, hydrocortisone acetate, hydrocortisone, butyrate, hydrocortisone hemisuccinate, hydrocortisone sodium succinate, hydrocortisone valerate, cortisone, cortisone acetate, dexamethasone, dexamethasone acetate, dexamethasone sodium phosphate, fluadrenolide, fludrocortisone, fludrocortisone acetate, flunisolide, flucinolone acetonide, flucinolone acetonide 21-acetate, fludinonide, fluorometholone, flumethasone pivalate, methylprednisolone, methylprednisolone acetate, methylprednisolone hemisuccinate, methylprednisolone sodium succinate, paramethasone, paramethasone acetate, prednacinolone, prednisolone, prednisolone acetate, prednisolone sodium phosphate, prednisone, triamcinolone, triamcinolone diacetate, and triamcinolone acetonide. This list is not considered comprehensive, and the listed corticosteroids are not necessarily considered to be equivalent to each other. It is simply stated that the above corticosteroids are suitable to accomplish the objectives of one embodiment of the present invention.

Where a local anesthetic compound is combined with the formulations including the Larrea genus extract, examples of suitable anesthetic compound include benzocaine, a benzocaine salt, cocaine, a cocaine salt, cocaine hydrochloride, cocaine nitrate, cocaine sulfate, lidocaine, a lidocaine salt, lidocaine hydrochloride, prilocaine, prilocaine hydrochloride, a prilocaine salt, procainamide hydrochloride, procaine, a procaine salt, procaine hydrochloride, tetracaine, tetracaine hydrochloride, and a tetracaine salt. This list is not considered comprehensive, and the listed anesthetics are not necessarily considered to be equivalent to each other. It is simply stated that the above anesthetics are suitable to accomplish the objectives of one embodiment of the present invention.

Where an NSAID is combined with the formulations including the Larrea genus extract, examples of a suitable NSAID include acetaminophen, aspirin, benzydamine, ibuprofen, indomethacin, ketoprofen, naproxen, naproxen sodium, and salicin. This list is not considered comprehensive, and the listed NSAIDs are not necessarily considered to be equivalent to each other. It is simply stated that the above NSAIDs are suitable to accomplish the objectives of one embodiment of the present invention.

Where a lipid or lipid-containing substance is combined with the formulations including the Larrea genus extract, examples of a suitable anti-inflammatory fatty acids include gamma-linolenic acid (GLA), eicosapentaenoic acid (EPA), docosahexaenoic acid (DHA), and alpha-linolenic acid (LNA).

Where a substance P antagonist is combined with the formulations including the Larrea genus extract, examples of a suitable substance P antagonist include capsaicin, capsicum extract, capsicum tincture, oleoresins capsicum, and an extract from a plant which is a species of the Capsicum genus.

The present invention may also comprise a method of treating human glioma cells, comprising administering to a human in need thereof, an effective amount of a pharmaceutical composition of an extract of *Larrea tridentate*.

The present invention may also comprise a method of treating viral diseases caused by viruses from the retrovirus family of viruses, the Hepatitis B virus, the Herpesviridae family of viruses, and viruses which require Sp1 class proteins to initiate viral replication, inflammatory diseases which are mediated by the effects of leukotrienes, and virally induced inflammation leading to postherpetic neuralgia, multiple sclerosis, Alzheimer's disease, cancer, including inhibition of human aromatase enzymes, atherosclerosis, hypertension, arteriosclerosis, and subsequent coronary artery disease using a nontoxic, therapeutic agent comprising an extract of *Larrea tridentate* plant material comprising NDGA and Mal. 4; and ascorbic acid, ascorbic acid esters (i.e. ascorbyl palmitate), and/or ascorbic acid salts (i.e. sodium ascorbate).

The extract may also include a corticosteroid compound, which may be selected from the above list, at a therapeutically effective concentration, generally 0.01 to 2.5% when the formulation is topically applied, and generally 5 to 60 milligrams per day for orally ingested steroids.

The extract may also include a local anesthetic compound, which may be selected from the above list, at a therapeutically effective concentration, generally about 1 to 30% when the formulation is topically applied.

The extract may also include an NSAID, which may be selected from the above list, at a therapeutically effective concentration.

The extract may also include an anti-inflammatory fatty acid, which may be selected from the above list, at a therapeutically effective concentration, generally about 1 to 20 grams per day for oral formulations, and about 1 to 80% (weight/weight) for topically applied formulations.

The extract may also include a substance P antagonist, which may be selected from the above list, at a therapeutically effective concentration, generally about 0.025 to 0.1% for the liquid base, lotion base or cream base containing the extract of Larrea tridentata.

BRIEF DESCRIPTION OF THE DRAWINGS

The accompanying drawings illustrate the present invention and are a part of the specification. Together will the following description, the drawings demonstrate and explain the principles of the present invention. In the drawings.

DETAILED DESCRIPTION OF THE PREFERRED EMBODIMENT

Figure 1:
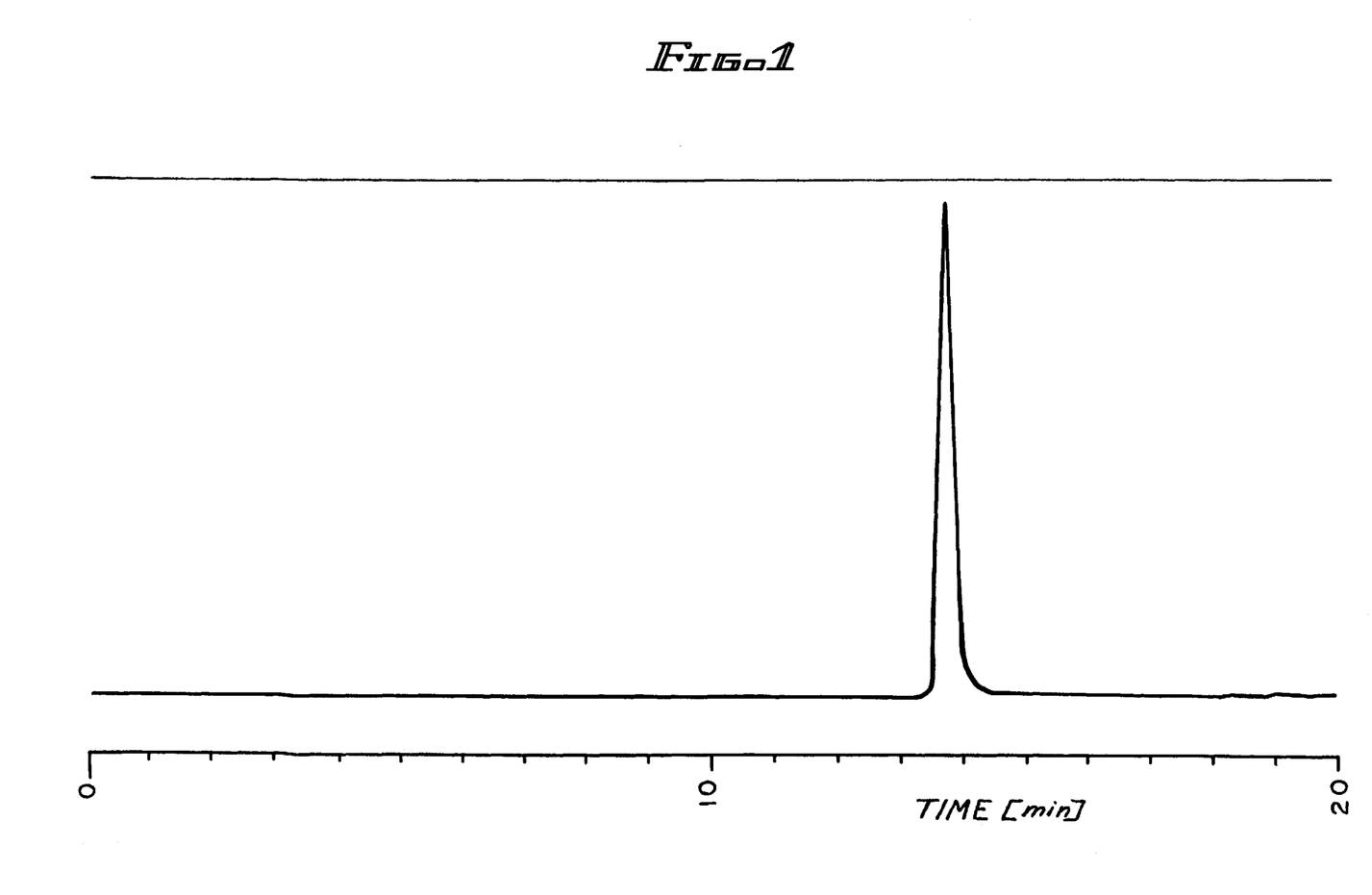
FIG. 1 is a high performance liquid chromatography ("HPLC") tracing of NDGA, as a purified compound (reported by the manufacturer to have a minimum purity of 90%). Slight amounts of unidentified impurities, probably methylated NDGA compounds, are indicated. However, no NDGA quinone is detectable in the sample. The tracing was taken at 280 nm absorbance.
Figure 2:
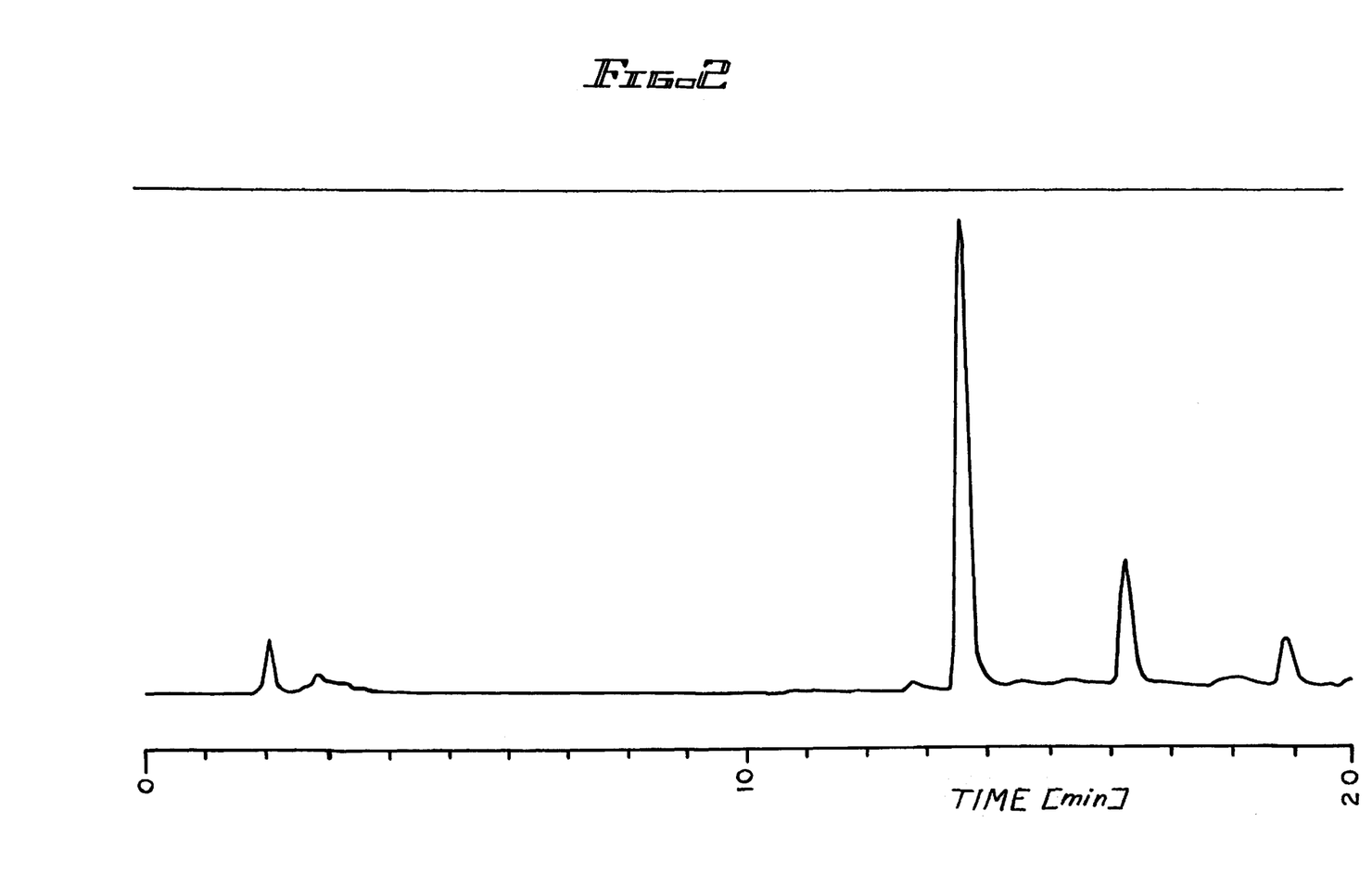
FIG. 2 is a HPLC tracing of NDGA as a purified compounds described in reference to FIG. 1 which has been treated with the strong oxidizing agents sulfuric acid and potassium dichromate. NDGA quinone, the oxidation product of NDGA, is identified in the chromatogram as the large peak at 16.5 minutes. The tracing was taken at 280 nm absorbance.
Figure 3:
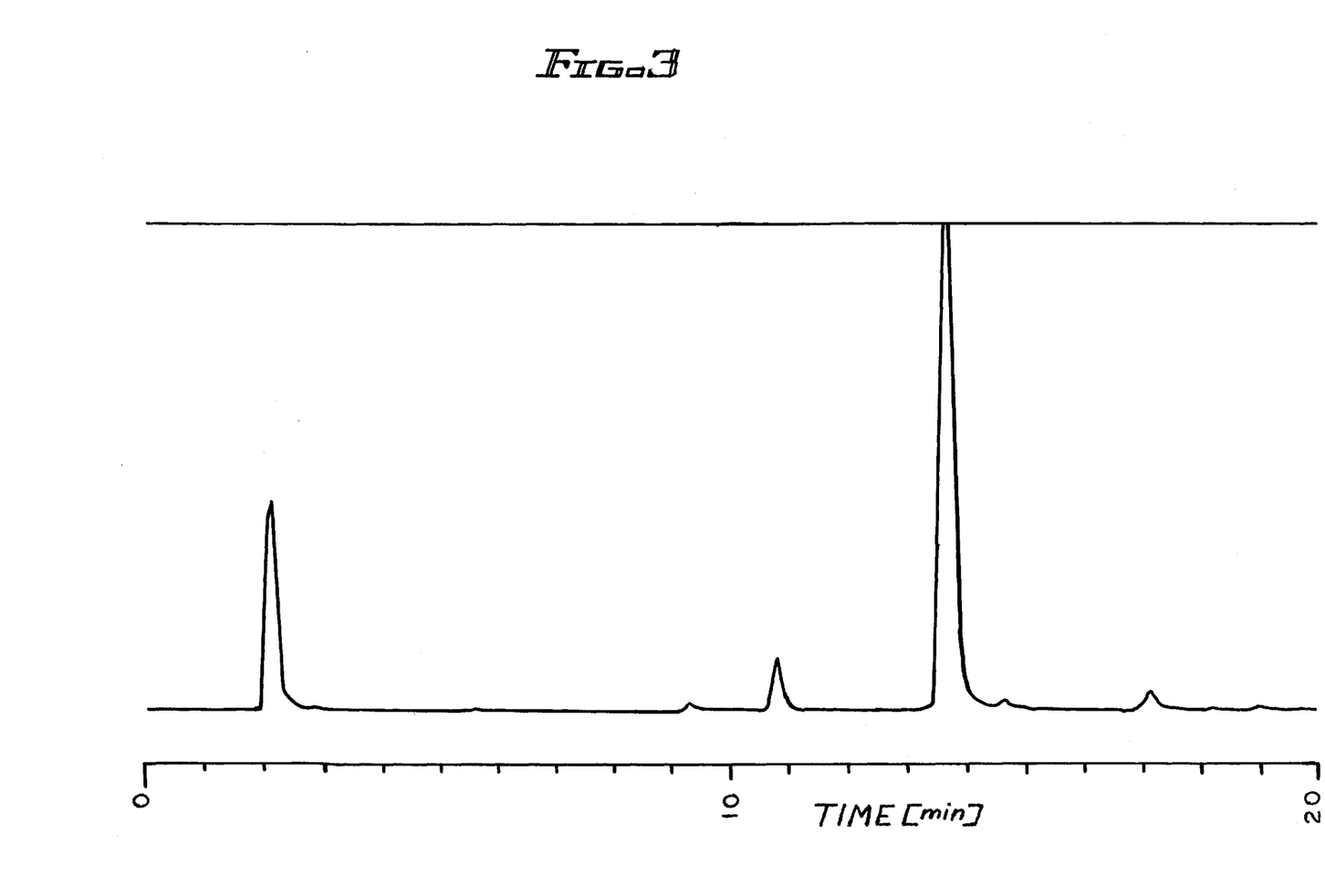
FIG. 3 is an HPLC tracing of a purified NDGA sample as described in reference to FIG. 1 and treated with oxidizing agents as described in reference to FIG. 2, and then treated according to the principles of the present invention, with the chemical reducing agent, ascorbic acid. NDGA quinone is not detectable at 16.5 minutes after treatment was completed. The tracing was taken at 280 nm absorbance.
Figure 4:
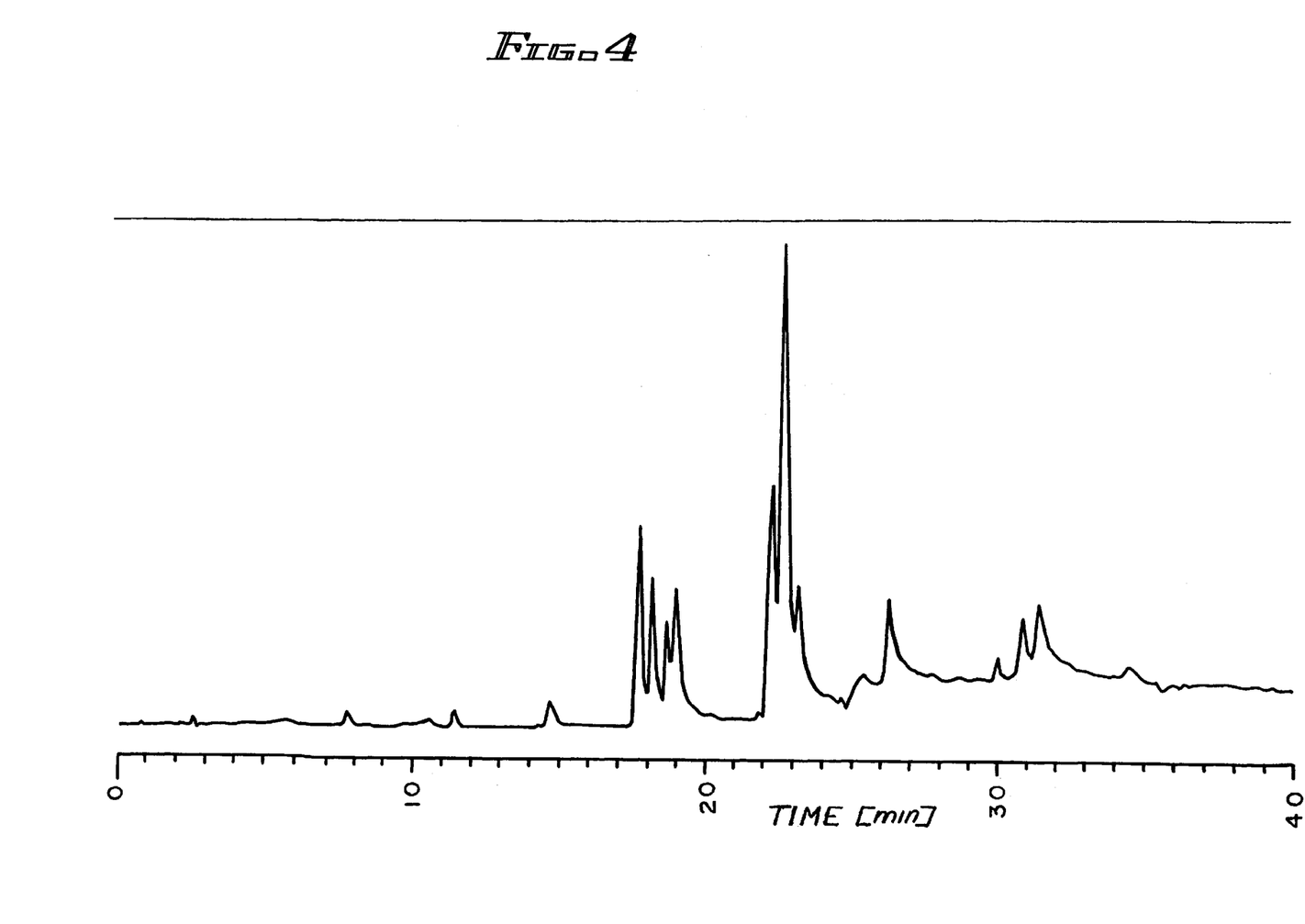
FIG. 4 is an HPLC tracing of a concentrated *Larrea tridentate* extract, which has been treated with the strong oxidizing agents sulfuric acids and potassium dichromate. A peak corresponding with NDGA quinone is identified in the chromatogram as the small peak occurring at 30 minutes. The tracing was taken at 375 nm absorbance.
Figure 5:
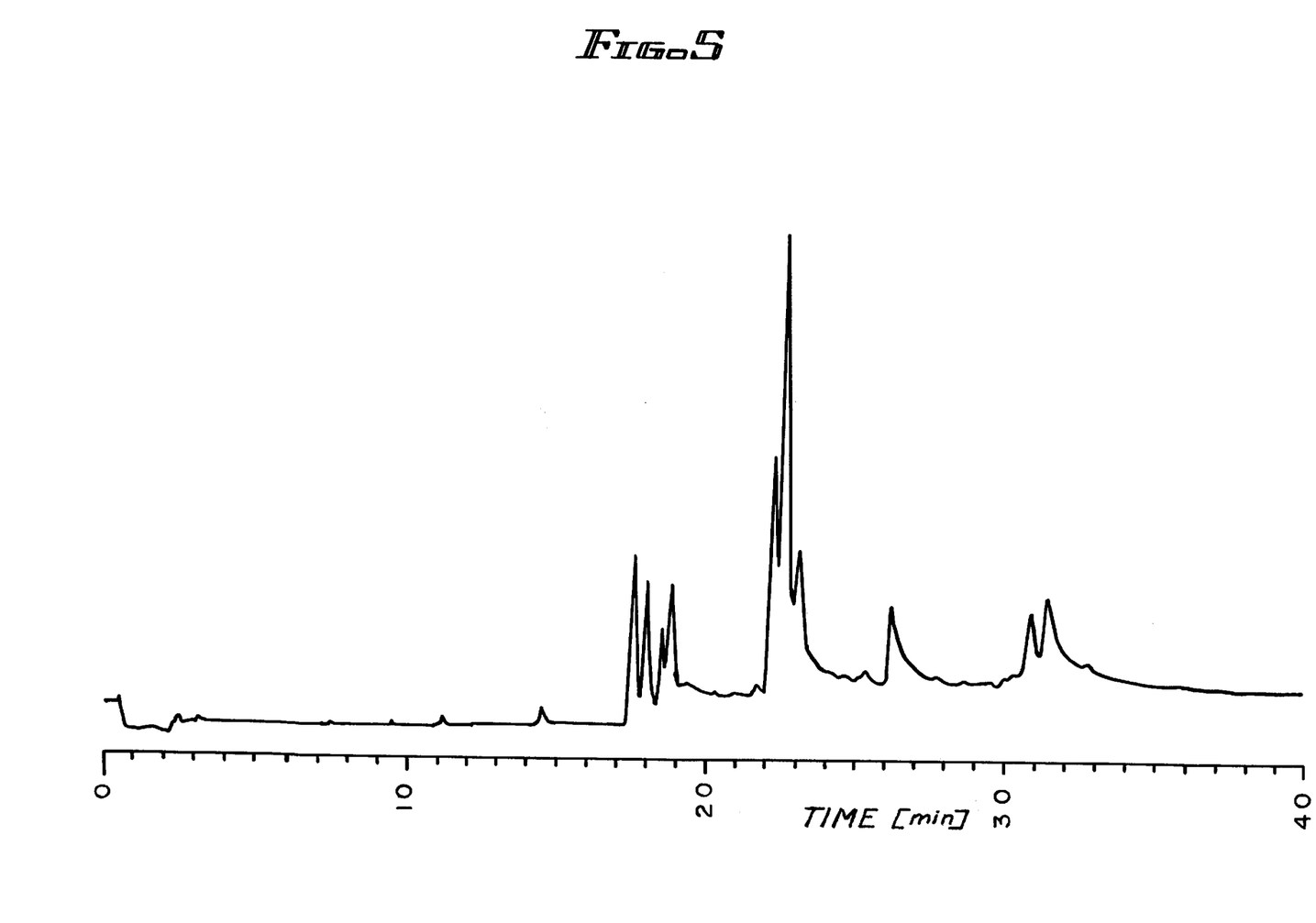
FIG. 5 is an HPLC tracing of a concentrated *Larrea tridentate* extract, produced according to the methods of the present invention. No NDGA quinone peak is observed at 30 minutes. The tracing was taken at 375 nm absorbance.

The present invention includes at least two products.

(1) a nontoxic extract of *Larrea tridentate* plant material having a high concentration of NDGA and little or no NDGA quinone which can be used as a therapeutic agent; and (2) NDGA, for use as a food additive or therapeutic agent, which does not oxidize into NDGA quinone during storage or processing.

An important principle of the invention is that ascorbic acid, when combined with NDGA, reduces any NDGA quinone present into NDGA, and prevent the NDGA from oxidizing and producing more NDGA quinone. Other compounds and agents may be theoretically used to reduce NDGA, and to prevent oxidation of NDGA into an oxidation product. Such agents include ascorbic acid esters (i.e. ascorbyl palmitate), ascorbic acid salts (i.e. sodium ascorbate), butylated hydroxyanisole (BHA), butylated hydroxytoluene (BHT), hydrogen sulfide, hypophosphorous acid (phosphinic acid), monothioglycerol (3 mercapto-1,2-propanediol), potassium bisulfite (potassium metabisulfite, potassium pyrosulfite), propyl gallate, sodium bisulfite (sodium metabisulfite, sodium pyrosulfite), sodium hydrosulfite (sodium dithionite), sodium thiosulfate (sodium hyposulfite), sulfur dioxide, sulfurous acid, a tocopherol, or vitamin E (DL-alpha-tocopherol). These agents are not necessarily considered to be equivalents to ascorbic acid, or each other, some having advantages not possessed by all the others. In fact, ascorbic acid was found to be an unexpectedly powerful reducing agent for converting NDGA quinone to NDGA. In laboratory tests, ascorbic acid, sodium hydrosulfite, and sodium bisulfite were added at 100 mg/nl to separate methanolic solutions of oxidized NDGA. Ascorbic acid proved to be the fastest reducing agent (approximately 1 minute). Subsequent chromatography of the mixtures showed that when sodium hydrosulfite or sodium bisulfite is used as the reducing agent, NDGA quinone is still detectable. However, when ascorbic acid is used, all traces of NDGA quinone are completely eliminated. Accordingly, ascorbic acid proved to be a better reducing agent than either sodium bisulfite or sodium hydrosulfite. This is an unexpected advantage as both sodium bisulfite and sodium hydrosulfite are strong reducing agents with reducing power considered as effective or more effective than the reducing power of ascorbic acid. Sodium hydrosulfite in fact has almost ten times the reduction potential of ascorbic acid. Accordingly, it is only asserted that each of the above listed agents could be used according to the principles of the invention as described in this specification to substantially accomplish the objects of the invention. The preferred embodiment of the invention will be described below.

According to the principles of the present invention, a nontoxic extract of Larrea tridentata having a high concentration of NDGA and very little or no NDGA quinone can be prepared by saturating the extract with ascorbic acid. Additional amounts of one of the ascorbic acid may be added to the extract or products formulated therefrom to inhibit the natural oxidation of component NDGA into NDGA quinone during processing and storage.

According to the preferred embodiment of the present invention, a nontoxic extract is prepared by the following method. *Larrea tridentate* plant material consisting mostly of whole leaves and stems, but also possibly containing a small amount of whole flowers and fruits, i.e. whole plant material, is air dried. The dried whole plant material is extracted using a suitable solvent. In the preferred embodiment, the solvent is an organic solvent, preferably acetone.

The organic solvent is recirculated three times over the correct ratio of plant material to completely dissolve the organic compounds on the surface of the plant material and to produce a crude *Larrea tridentate* extract. The resulting crude extract is filtered through cellulosic media (i.e. qualitative grade filter paper) to remove dirt and particulates. A chemical emulsifying and stabilizing agent, Food Chemicals Codex (F.C.C.) grade polysorbate 80, is added to the clarified extract at a concentration of 0.01% by volume.

The clarified extract is then passed through a bed of ascorbic acid powder (5 grams of F.C.C. grade ascorbic acid powder for each liter of extract passed through) in a manner which facilitates contact of the extract with the ascorbic acid powder and results in saturation of the extract with ascorbic acid. Saturating the extract with the chemical reducing agent, ascorbic acid results in conditions which favor the chemical reduction of the toxic, oxidative metabolites of NDGA, which are present in *Larrea tridentate* plant tissues and the resulting extracts. By chemically reacting with the ascorbic acid, the toxic NDGA quinones are reduced to NDGA hydroquinone which is NDGA itself.

To concentrate the *Larrea tridentate* organic extract which is saturated with ascorbic acid, the extract is transferred to a water jacketed, stainless steel tank, which is heated to approximately 100 degrees C. by circulation of a suitable solvent (i.e. water). While the extract is heated in the tank, the organic solvent is boiled out of the extract and may be recovered by condensation for reuse. The extract is heated in the tank to approximately 10 degrees above the boiling point of the organic extraction solvent. This rise in temperature of the extract indicates that the concentrated *Larrea tridentate* extract is substantially free of the extraction solvent. The concentrated extract, approximately ¹/₁₀ the volume of the original *Larrea tridentate* extract, is then removed from the tank and packaged in tightly sealed plastic drums for storage and shipping.

Another aspect of the present invention includes mixing the concentrated Larrea tridentata extract with effective, additional amounts of ascorbic acid. Formulation of the extract with excess amounts of ascorbic acid prevents subsequent formation of NDGA quinone during subsequent processing, storage, and formulating of the extract, and functions as a synergistic antioxidant in vivo with NDGA and other endogenous antiviral compounds.

A further aspect of the present invention includes mixing the concentrated *Larrea tridentate* extract with therapeutically effective amounts of at least one anti-inflammatory corticosteroid compound. This may be accomplished by a direct mixing of the corticosteroid compound, preferably prednisone for oral formulations and betamethasone dipropionate for topical formulations, at the proper concentration, generally 0.1 to 2.5% for topically applied corticosteroids and generally 5 to 60 milligrams per day for orally ingested steroids, with the liquid base, lotion base, cream base or dry excipient ingredients containing the extract of *Larrea tridentate*. To assist with uniform dispersion of the corticosteroid compound into the liquid base, lotion base, cream base or dry excipient ingredients, the corticosteroid compound may be dissolved or dispersed in a suitable, pharmaceutically acceptable solvent, preferably USP/NF grade anhydrous ethanol, prior to mixing in to the liquid base, lotion base, cream base or dry excipient ingredients. Additionally, the mixture resulting from the formulations containing dry excipient materials can be prepared in a manner suitable for milling into a uniform powder and encapsulation in standard, hard gelatin capsules.

Still a further aspect of the present invention includes addition of a local anesthetic to the concentrated extract of *Larrea tridentate*, at a therapeutically effective concentration. This may be accomplished by direct mixing of the anesthetic compound, preferably lidocaine base, at the proper concentration, generally 1 to 30% concentration, with the liquid base, lotion base or cream base containing the extract of Larrea tridentata. To assist with uniform dispersion of the anesthetic compound, the anesthetic compound may be dissolved or dispersed in a suitable, pharmaceutically acceptable solvent, preferably USP/NF grade isopropanol, prior to mixing into the liquid base, lotion base, or cream base. Liquid, lotion and cream based formulations, containing pharmaceutically ingredients, may be used for topical application to regions of the body affected by herpes virus infections.

Another aspect of the present invention includes addition of a non-steroidal anti-inflammatory compound (NSAID) at a therapeutically effective concentration, to the concentrated extract of *Larrea tridentate*. This may be accomplished by direct mixing of the NSAID, preferably benzydamine at 3% (weight/weight) concentration for topical formulations, and ibuprofen at 100 milligrams per 50 milligrams of *Larrea tridentate* extract for oral formulations, with the liquid base, lotion base, cream base or dry excipient ingredients containing the extract of *Larrea tridentate*. To assist with uniform dispersion of the NSAID into the liquid base, lotion base, cream base or dry excipient ingredients, the NSAID may be dissolved or dispersed in a suitable, pharmaceutically acceptable solvent, preferably USP/NF grade ethanol, prior to mixing in to the liquid base, lotion base, cream base or dry excipient ingredients. Additionally, the mixture resulting from the formulations containing dry excipient materials can be prepared in a manner suitable for milling into a uniform powder and encapsulation in standard, hard gelatin capsules.

Another aspect of the present invention includes addition of a lipid or lipid containing substance at a therapeutically effective concentration, to the concentrated extract of *Larrea tridentate*. The lipid or lipid containing substance may include at least one of the anti-inflammatory fatty acids, GLA, EPA, DHA, and LNA. This can be accomplished by direct mixing of the lipid or lipid containing substance, preferably marine fish oils that are rich in EPA and DHA or flax seed oil which is rich in LNA, at about 1 to 20 grams per day for oral formulations, and about 1 to 80% (weight/weight) for topically applied formulations, with the liquid base, lotion base, cream base or dry excipient ingredients containing the extract of *Larrea tridentate*. Additionally, the resulting liquid formulations may be encapsulated in soft gelatin capsules and the mixture resulting from the formulations containing dry excipient materials can be prepared in a manner suitable for milling into a uniform powder and subsequent tableting or encapsulation in standard, hard gelatin tablets.

Yet another aspect of the present invention includes addition of a substance P antagonist at a therapeutically effective concentration, to the concentrated extract of *Larrea tridentate*. This can be accomplished by direct mixing of the substance P antagonist, preferably natural capsaicin, at the proper therapeutic concentration, generally 0.025 to 0.1%, with the liquid base, lotion base or cream base containing the extract of *Larrea tridentate*. To assist with uniform dispersion of the substance P antagonist into the liquid base, lotion base or cream base, the substance P antagonist, preferably natural capsaicin, may be dissolved or dispersed in a suitable, pharmaceutically acceptable solvent, preferably USP/NF grade isopropanol, prior to mixing in to the liquid base, lotion base or cream base. Liquid, lotion and cream based formulations, containing pharmaceutically ingredients, may be used for topical application to regions of the body affected by herpes virus infections.

The present invention is based in part on the discovery that a *Larrea tridentate* extract, which is produced according to the methods of the present invention, contains no detectable amount of NDGA quinone when analyzed by high performance liquid chromatography. Because of the foregoing discussion linking NDGA quinone with the toxic effects associated with the consumption of *Larrea tridentate* products, the production of *Larrea tridentate* extract, with a very low concentration of NDGA quinone, for use in medical formulations is very important.

Further, experiments performed by the inventors show that formulations based on the *Larrea tridentate* extract and ascorbic acid compound, as described in this invention, have pronounced antiviral activity against Herpes simplex virus types 1 and 2, and against Kaposi's Sarcoma in human patients. Experimentation has also shown that the described formulations have pronounced antiviral activity against Herpes simplex virus type 1 (HSV-1) in both animal cell culture models and human volunteers as well as anti-inflammatory action in human volunteers.

Also, as previously mentioned, the non-toxic extract of *Larrea tridentate*, prepared according to the above described methods, contains an abundance of biologically active lignans and flavonoids. Because of the chemical similarities between the flavonoids and lignans tested in the scientific publications cited previously, and the phenolic compounds (predominantly lignans and flavonoids) contained in the non-toxic extract of *Larrea tridentate* of the present invention, extracts of *Larrea tridentate* can function as inhibitors of human aromatase enzymes.

Based on the composition of lignans and flavonoids in *Larrea tridentate* extract and the fact that lipophyllic compounds such as lignans and flavonoids tend to concentrate in fatty tissues, such as adipose tissue, a pharmaceutically useful dosage for the partial inhibition of aromatase in human preadipocyte tissues can be as low as 100 to 500 milligrams of *Larrea tridentate* extract per day taken over the course of several years prior to the onset of menopause. In this way, supplementation with a small dose of *Larrea tridentate* extract, only several hundred milligrams per day prior to the onset of menopause, can significantly decrease aromatase levels in human preadipocyte tissues and thereby prevent or diminish the incidence of breast cancer in these individuals.

The present invention therefore provides methods for the medically useful and effective extract of *Larrea tridentate* and formulations for production of pharmaceutical agents which have immediate and commercially important utility in the medical treatment of viral and inflammatory diseases.

Experimental Results

The following are provided by way of illustrating examples of extraction and processing formulations of the *Larrea tridentate* extract, and are provided by way of illustration only and are not intended to limit the invention in any way.

EXAMPLE 1

Plant material (consisting of mostly leaves but with some small branches and a small amount of fruits and flowers) was harvested from *Larrea tridentate* shrubs growing in the Arizona desert, southwest of Gila Bend, Arizona. The plant material was air dried in the shade at ambient temperature and humidity for one week before processing. 100 kg of plant material was extracted with 100 liters of F.C.C. grade acetone by recirculating the acetone over the plant material three times. The resulting Larrea tridentata extract was filtered through Whatman #1 filter paper.

5 mils of F.C.C. grade polysorbate 80 was added to 50 liters of the extract and the extract was slowly passed through a glass column packed with 250 g of powdered ascorbic acid. The extract, saturated with ascorbic acid, was concentrated by boiling off the acetone solvent in a water-jacketed stainless steel tank, which was heated to approximately 100 degrees Celsius by circulating hot water. The resulting concentrated extract, in the form of a viscous liquid, was collected in plastic drums and used to prepare medical formulations.

A further formulation was prepared by adding betamethasone dipropionate at a concentration of 0.05% (weight/weight) to a 3% *Larrea tridentate* extract lotion prepared according to the principles of the present invention, in a pharmaceutically acceptable lotion base. This novel combination of a natural antiviral agent and an anti-inflammatory corticosteroid was produced for use by human volunteers and in clinical trials.

A further formulation was prepared by adding prednisone at a concentration of 10 milligrams per capsule to a *Larrea tridentate* extract prepared according to the principles of the present invention, where the *Larrea tridentate* extract is also encapsulated at 50 milligrams per capsule, along with pharmaceutically acceptable excipients. This novel combination of a natural antiviral agent and an anti-inflammatory corticosteroid was produced for use by human volunteers and in clinical trials.

A further formulation was prepared by adding lidocaine at a concentration of 5% (weight/weight) to a 3% *Larrea tridentate* extract lotion prepared according to the principles of the present invention, in a pharmaceutically acceptable lotion base. This novel combination of a natural antiviral agent and an anesthetic compound was produced for use by human volunteers and in clinical trials.

A further formulation was prepared by adding benzydamine at 3% (weight/weight) to a 3% *Larrea tridentate* extract lotion prepared according to the principles of the present invention, in a pharmaceutically acceptable lotion base. This novel combination of a natural antiviral agent and an NSAID was produced for use by human volunteers and in clinical trials.

A further formulation was prepared by adding ibuprofen at a concentration of 100 milligrams per capsule to a *Larrea tridentate* extract prepared according to the principles of the present invention, where the *Larrea tridentate* extract is also encapsulated at 50 milligrams per capsule, along with pharmaceutically acceptable excipients. This novel combination of an NSAID agent and an anti-inflammatory corticosteroid was produced for use by human volunteers and in clinical trials.

A further formulation was prepared by adding flax seed oil at a concentration of 10% (weight/weight) to a 3% *Larrea tridentate* extract lotion prepared according to the principles of the present invention, in a pharmaceutically acceptable lotion base. This novel combination of a natural antiviral agent and a natural lipid compound containing an anti-inflammatory fatty acid, LNA, was produced for use by human volunteers and in clinical trials.

A further formulation was prepared by adding marine fish oil at a concentration of 250 milligrams per capsule to a *Larrea tridentate* extract prepared according to the principles of the present invention, where the *Larrea tridentate* extract is also encapsulated at 50 milligrams per capsule, along with pharmaceutically acceptable excipients. This novel combination of a natural lipid compound containing the anti-inflammatory fatty acids, EPA and DHA, was produced for use by human volunteers and in clinical trials.

A further formulation was prepared by adding natural capsaicin at a concentration of 0.025% (weight/weight) to a 3% *Larrea tridentate* extract lotion prepared according to the principles of the present invention, in a pharmaceutically acceptable lotion base. This novel combination of a natural antiviral agent and a natural lipid compound containing a substance P antagonist, was produced for use by human volunteers and in clinical trials.

EXAMPLE 2

Several formulations of concentrated Larrea extract suitable for encapsulation were prepared by thoroughly mixing the concentrated extract, according to the methods of the present invention, with dry excipient materials including starch, sucrose, fructose, and ascorbic acid powder. In some cases, other ingredients including antiviral and anti-inflammatory agents or herbal extracts i.e. Echinacea, Podophyllin, etc. were also combined in formulations. In all cases, the mixtures consisted of one part concentrated *Larrea tridentate* extract with 5 to 10 parts dry excipient material. These formulations were used to treat HIV opportunistic infections, and Herpes virus infections described in this specification. The treatment consisted of administering several capsules containing 50 to 100 mg of *Larrea tridentate* extract per capsule which were ingested daily.

EXAMPLE 3

Several formulations of concentrated *Larrea tridentate* extract in a lotion base were prepared by adding the concentrated extract, as produced in example 1, into various lotion formulations. The concentration of extract added to the lotion base can range from 0.1 to 5% volume/volume. In initial trial with human volunteers, a 3% lotion prepared according to the principles of the present invention has been used successfully in the medical treatment of athletes foot, viral lesions caused by herpes simplex virus (HSV-1, HSV-2), Kaposi's Sarcoma, and inflammation of the skin induced by contact allergens, ultraviolet light and thermal exposure. The treatment consisted of applying the lotion frequently and liberally to the affected areas.

EXAMPLE 4

Results obtained by the inventors show that the concentrated Larrea extract, produced by the methods of the present invention, when used at a concentration greater than 20 micrograms per milliliter, is nearly 100% effective in protecting African Green Monkey kidney cells from destruction by the Herpes simplex-1 virus (HSV-1).

It is apparent from the evidence presented above that the methods and compositions of the present invention meet long-standing needs in the medical treatment of viral and inflammatory diseases.

EXAMPLE 5

Extracts of *Larrea tridentate*, prepared according to the methods of the present invention, have been shown to strongly inhibit the typical cytopathic effects of a standard strain of varicella-zoster virus obtained from the American Type Culture Collection (ATCC). Confluent cultures of Human Epithelial Cells (HEp2) and Monkey Kidney Cells (Vero) were infected with varicella-zoster virus and then either treated with 10 micrograms per milliliter of *Larrea tridentate* extract or left untreated. The cells treated with the *Larrea tridentate* extract showed a considerable inhibition of cytopathic effects (four-fold drop in titer) compared to the untreated cells after 10 days in culture.

EXAMPLE 6

Extracts of Larrea tridentata, prepared according to the methods of the present invention, have been shown to possess pronounced antiviral and anti-inflammatory properties when tested with human subjects. Reports by clinicians using these formulations show effective resolution of disease conditions caused by herpes viruses including: herpes simplex 1, herpes simplex 2 (genital herpes), herpes zoster, and Kaposi's Sarcoma (human herpes virus 8). The fast and complete success in treating most of the herpes virus infections with Larrea-based formulations performed well where all other therapies including Zovirax and aggressive radiation therapy had failed. Also, significant in the clinical reports is the fact that extracts of *Larrea tridentate* were safe and effective for treating various herpes virus infections in immonocompromised individuals including HIV positive individuals and people with AIDS. Accordingly, Larrea-based antiviral therapy is shown to be superior to currently available prescription antiviral drug therapy, since widely-used antiviral drugs like acyclovir are often not considered practical in treating herpes virus infections in immunocompromised individuals.

EXAMPLE 7

A human glioma cell line was used to assess the efficacy of an extract of *Larrea tridentate*, prepared according to the principles of the present invention, to kill tumor cells. The cells were derived from a glioblastoma multiforme and cultured to become a drug resistant line. These same cells have survived treatments of 70 ug/ml BCNU, currently, the most common chemotherapeutic agent used in the treatment of glioblastoma multiforme (cell line obtained from Barrow Neurological Institute, Phoenix, Ariz.). An in vitro MTT was utilized to assess the *Larrea tridentate* extract's affect on growth and survival of the tumor cells. Cells were plated at a concentration of 2.000 cells per well in 96 well dishes. Varying concentrations of the *Larrea tridentate* extract solution were applied to the cells on day 1, ranging from 5 micrograms per milliliter to 125 micrograms per milliliter. 5 replicate wells of each drug concentration were analyzed. Cells were observed on Days 1, 3, 6 and 9 after drug treatment. Absorbance values directly correlate to cell survival and growth by MTT assay.

Significant decrease in tumor cell growth and survival was noted on day 3, when almost 90% of the tumor cells, which were treated with greater than or equal to 25 ug/ml of the *Larrea tridentate* extract, were killed. Based on these results, a one day exposure to the *Larrea tridentate* extract was sufficient to produce significant anti-tumorigenic effects on a drug resistant, human glioma cell line, after 3 days, in vitro. These results indicate that the *Larrea tridentate* extract may be an effective agent for the treatment of human gliomas, especially those showing resistance to traditional chemotherapeutic agents. Based on this experimental data and data regarding the chemical composition of *Larrea tridentate* extract prepared according to the principles of the present invention, a pharmaceutically useful dosage for the treatment of brain tumors could be as low as 5 to 25 micrograms per gram of body weight or 340 to 1700 milligrams for an average 68 kilogram man.

EXAMPLE 8

Experiments performed at the University of California Davis School of Medicine, Division of Rheumatology/Allergy and Clinical Immunology, demonstrate the Larrea tridentata extract to be a powerful stimulator of interleukin-6 (IL-6) production in blood monocytes. The *Larrea tridentate* extract also functions as a weak stimulator of interleukin-1 (IL-1) and a weak inhibitor of interleukin-2 (IL-2), which might also be of importance when developing immunological therapies.

In vitro tests performed at UC Davis demonstrate that, at a concentration of 50micrograms per milliliter, the *Larrea tridentate* extract significantly increased the production of IL-6 in both phytohemaglutinin (PHA) stimulated cells and native cells (not stimulated with PHA). Increases in IL-6 production were as much as 70+% in native cells and as much as 150+% in PHA stimulated cells. According to Dr. M. Eric Gershwin, M.D., Chief of the Division of Rheumatology/Allergy and Clinical Immunology, this nontoxic extract of *Larrea tridentate* is one of the most powerful stimulators of IL-6 production tested at his laboratory.

Stimulators of IL-6 production have utility for stimulating the immune responses for treatment of infections (including viral infections), cancer, immunosupressive disorders (including AIDS and chronic fatigue syndrome) and physical trauma (including burns). This immune system-enhancing activity, combined with the powerful anti-viral activity of the *Larrea tridentate* extract, makes it a very useful compound for the treatment of viral infections in general (including herpes viruses), as well as cancer, immunosupressive conditions (including AIDS) and physical trauma.

Many alternatives to the most preferred embodiment, described above, are also part of the present invention. For example, when the NDGA quinone is reduced using ascorbic acid in a *Larrea tridentate* extract, it is not crucial to add further amounts of ascorbic acid as described. While doing so provides a more stable nontoxic product, if additional amounts of one or more of these listed reducing agents are not added, the resulting extract will still have use as a nontoxic therapeutic agent.

Moreover, it is not crucial to use any of the listed reducing agents to reduce the NDGA quinone present initially in the extract. If another, perhaps even toxic, reducing agent is used to reduce the NDGA quinone naturally occurring in the *Larrea tridentate* extract, ascorbic acid can then be added to the resulting product to produce a nontoxic extract which will not develop quantities of NDGA quinone through oxidation during processing and storage. In such a process, an additional step to remove the reducing agent would likely be necessary.

Finally, as noted in the prior art NDGA has many known uses as an antioxidant food additive and as a therapeutic agent. NDGA for these purposes can be produced by extraction from natural sources, such as the *Larrea tridentate*, or can be synthesized. However the NDGA is produced, during processing and storage it oxidizes to produce NDGA quinone and is therefore toxic when ingested. Accordingly, it is within the scope of the invention to combine NDGA, whether extracted or synthesized, with ascorbic acid to produce a stable, nontoxic NDGA product that can be used as a food additive or therapeutic agent.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A herpes treatment agent comprising a concentrated extract of reduced NDGA-containing *Larrea tridentate* plant material and ascorbic acid, wherein the NDGA is reduced as a result of a chemical reaction between said extract and said ascorbic acid such that said ascorbic acid is provided at a concentration sufficient to saturate said extract prior to the concentration of said extract; and a compound selected from the group consisting of a corticosteroid, an anesthetic, a nonsteroidal anti-inflammatory, an anti-inflammatory fatty acid and a substance P antagonist.

2. The agent of claim 1, in the form of a lotion or a liquid.

3. A method of treating herpes lesions comprising applying to the affected area of a human in need thereof, an effective amount of the agent of claim 1.

4. A method of treating herpes lesions comprising applying to the affected area of a human in need thereof, an effective amount of a pharmaceutical composition comprising an extract of *Larrea tridentate* wherein said herpes lesions are symptoms of a herpes virus selected from the group comprising Herpes simplex virus 1, Herpes simplex virus 2, varicella-zoster virus (HHV-3), Epstein-Barr Virus (HHV-4), Cytomegalovirus (HHV-5), the roseoloviruses (HHV-6 and HHV-7), and HHV-8.

5. The method of claim 4, wherein said herpes virus is varicella zoster virus, exhibited as shingles.

6. A method of treating herpes virus comprising applying to the affected area of a human in need thereof, an effective amount of a pharmaceutical composition comprising an extract of *Larrea tridentate* wherein said herpes virus is selected from a group comprising Herpes simplex virus 1, Herpes simplex virus 2, vahrcella-zoster virus (HHV-3), Epstein-Barr Virus (HHV-4), Cytomegalovirus (HHV-5), and the roseoloviruses (HHV-6 and HHV-7) and HHV 8.

7. The method of claim 6, wherein said herpes virus is varicella-zoster virus, and said varicella zoster virus is exhibited as shingles.

8. A method of treating herpes virus comprising applying to the affected area of a human in need thereof, an effective amount of a pharmaceutical composition comprising and extract of *Larrea tridentate* wherein said herpes virus is exhibited a s postherpetic neuralgia.

9. A method for treating glioma tumors in humans, comprising administering to a human in need thereof, an effective amount of a composition comprising a concentrated extract of a reduced NDGA-containing *Larrea tridentate* plant material and ascorbic acid, wherein the NDGA is reduced as a result of a chemical reaction between said extract and said ascorbic acid such that said ascorbic acid is provided at a concentration sufficient to saturate said extract prior to the concentration of said extract.

10. The method of claim 9, wherein said effective amount is between about 5 and about 25 micrograms per gram of a body weight of said human.

11. The method of claim 9, wherein said effective amount is between about 340 milligrams and about 1700 milligrams.

12. A method for treating breast cancer in humans, comprising administering to a human in need thereof, an effective amount of a composition comprising a concentrated extract of a reduced NDGA-containing *Larrea tridentate* plant material and ascorbic acid, wherein the NDGA is reduced as a result of a chemical reaction between said extract and said ascorbic acid such that said ascorbic acid is provided at a concentration sufficient to saturate said extract prior to the concentration of said extract.

13. The method of claim 12, wherein between about 100 and about 500 milligrams of said extract of *Larrea tridentata* is administered per day.

14. A method for the stimulation of immune function in a human, comprising enhancing IL-6 production by administering to a human in need thereof an effective amount of a treatment agent comprising a concentrated extract of *Larrea tridentate* plant material.

15. The method of claim 14, wherein said stimulation of immune functions treats an inflammatory effect of a systemic viral disease.

16. The method of claim 15, wherein said systemic viral disease is herpes.

17. The method of claim 14, wherein said stimulation of immune functions treats an inflammatory effect of cancer.

18. The method of claim 14, wherein said stimulation of immune functions treats an inflammatory effect of physical trauma.

19. The method of claim 14, wherein said stimulation of immune functions treats an inflammatory effect of chronic fatigue syndrome.

* * * * *